United States Patent [19]

Sartorelli et al.

[11] Patent Number: 5,214,068
[45] Date of Patent: May 25, 1993

[54] SULFONYLHYDRAZINES AND THEIR USE AS ANTINEOPLASTIC AGENTS AND AS ANTITRYPANOSOMAL AGENTS

[75] Inventors: Alan C. Sartorelli, Woodbridge; Alan A. Divo, Branford; Krishnamurthy Shyam, Hamden; Philip G. Penketh, New Haven, all of Conn.

[73] Assignee: Yale University, New Haven, Conn.

[21] Appl. No.: 851,384

[22] Filed: Mar. 12, 1992

Related U.S. Application Data

[62] Division of Ser. No. 403,533, Sep. 6, 1989, Pat. No. 5,101,072.

[51] Int. Cl.$^5$ .............................................. A61K 31/18
[52] U.S. Cl. .................................. 514/601; 514/602; 514/603
[58] Field of Search ........................ 514/601, 602, 603

Primary Examiner—Jerome D. Goldberg
Attorney, Agent, or Firm—Sprung Horn Kramer & Woods

[57] ABSTRACT

Sulfonylhydrazines of the formula $RSO_2N(CH_2CH_2X)N(SO_2CH_3)_2$, wherein R is an alkyl or an aryl and X is a halogen or $OSO_2Y$, wherein Y is an alkyl or an aryl. Such sulfonylhydrazines are useful in treating cancer.

Methylating agents of the formula
(a) $R'SO_2N(CH_3)N(SO_2CH_3)_2$, wherein R' is an alkyl or an aryl and
(b) $R''SO_2N(CH_3)N(CH_3)SO_2R''$, wherein R'' is an alkyl or an aryl.

Such methylating agents are useful as antitrypanosomal and anticancer agents.

7 Claims, No Drawings

SULFONYLHYDRAZINES AND THEIR USE AS ANTINEOPLASTIC AGENTS AND AS ANTITRYPANOSOMAL AGENTS

GOVERNMENT RIGHTS

This invention was made with United States government support under Grant CA-02817 from the United States Public Health Service. The United States government may have certain rights in the present invention.

This is a division of application Ser. No. 07/403,533, filed Sep. 6, 1989, now U.S. Pat. No. 5,101,072.

BACKGROUND OF THE INVENTION

1. Field of the Invention

The present invention is directed to novel sulfonylhydrazines and their use as antineoplastic agents. The present invention also concerns methylating agents, especially N-methyl-N-sulfonylhydrazines, and their use as antineoplastic and trypanocidal agents.

2. Background Information

The synthesis and anticancer activity of a series of 1,2-bis(sulfonyl)-1-methylhydrazines was reported in K. Shyam, R. T. Hrubiec, R. Furubayashi, L. A. Cosby and A. C. Sartorelli, *J. Med. Chem.*, 30, 2157–2161 (1987). Base-catalyzed decomposition to generate the putative methylating species $RSO_2N=NMe$ was hypothesized to account for the observed biological activity.

Trypanosomes of the brucei group are flagellated protozoa which produce lethal infections in humans and domestic mammals throughout much of sub-Saharan Africa. (M. Katz, D. D. Despommier and R. W. Gwadz, *Parasitic Diseases*, Springer-Verlag, New York (1982); R. Allsopp, D. Hall and T. Jones, *New Scientist*, 7, 41–43 (1985); C. A. Hoare, *Adv. Parasitol.*, 5, 47–91 (1967)). With the exception of alpha-difluoromethylornithine (DFMO), the trypanocidal drugs currently in use have been available for 25 to 80 years. Current treatment of early-stage infections consists of suramin for *T. rhodesiense* and pentamidine for *T. gambiense* (S. R. Meshnick, "The Chemotherapy of African Trypanosomiasis", In: *Parasitic Diseases*, J. M. Mansfield, ed., Marcel Dekker, Inc., New York (1984); F.I.C. Apted, *Manson's Tropical Diseases*, 18th edition, Bailliere Tindall, Eastbourne (1983), pp. 72–92; W. E. Gutteridge and G. H. Coombs, *The Biochemistry of Parasitic Protozoa*, Macmillan, London (1977), pp. 1–25).

These therapies require approximately six weeks of hospitalization due to drug toxicity. The only drug available for late-stage sleeping sickness is melarsoprol (S. R. Meshnick, supra). This drug has serious side-effects and up to 5% of patients die due to drug toxicity. Suramin, pentamidine and melarsoprol are all administered by intravenous injection. Recently, DFMO has been shown to be effective against early-stage sleeping sickness in man and animals. However, there are doubts as to its efficacy in late-stage disease unless it is used in combination with other less desirable agents such as bleomycin (P. P. McCann, G. J. Bacchi, A. B. Clarkson, Jr., J. R. Seed, H. C. Nathan, B. O. Amole, S. H. Hutner and A. Sjoerdsma, *Medical Biol.*, 59, 434–440 (1983); A. B. Clarkson, Jr., C. J. Bacchi, G. H. Mellow, H. C. Nathan, P. P. McCann and A. Sjoerdsma, *Proc. Natl. Acad. Sci. USA*, 80, 5729–5733 (1983)). Therefore, better drugs are needed to treat trypanosomiasis.

SUMMARY OF THE INVENTION

The present invention concerns sulfonylhydrazine compounds of the formula $RSO_2N(CH_2CH_2X)N(SO_2CH_3)_2$, wherein R is an alkyl having 1 to 10 carbon atoms, preferably 1 to 6 carbon atoms and preferably methyl, ethyl, n-propyl, i-butyl or n-butyl, cycloalkyl, preferably having 3 to 6 carbon atoms, or an aryl, preferably having 6 to 12 carbon atoms, for example, phenyl, 4-tolyl, 4-methoxyphenyl, 4-chlorophenyl, 4-bromophenyl, 4-nitrophenyl, naphthyl or biphenyl and X is a halogen selected from the group consisting of F, Cl, Br and I, especially Cl, Br or I, or $OSO_2Y$, wherein Y is an unsubstituted or substituted alkyl having 1 to 10 carbon atoms or an unsubstituted or substituted aryl. Y is preferably methyl, but non-limiting examples of Y also include ethyl, propyl, isopropyl, trichloromethyl, trifluoromethyl, phenyl, p-tolyl, p-methoxyphenyl, p-chlorophenyl and other substituted phenyls. A preferred compound is $CH_3SO_2N(CH_2CH_2Cl)N(SO_2CH_3)_2$.

The present invention also relates to a method of treating cancer (e.g., leukemias, lymphomas, breast carcinoma, colon carcinoma and lung carcinoma), in a warm-blooded animal patient, e.g., a human, by administering to such patient an antineoplastic effective amount of the aforesaid sulfonylhydrazine.

The present invention is also directed to the following two classes of methylating agents:

(1) $R'SO_2N(CH_3)N(SO_2CH_3)_2$, namely 1,2,2-tris(sulfonyl)-1-methylydrazines, wherein R' is an alkyl having 1 to 10 carbon atoms, preferably 1 to 6 carbon atoms and preferably methyl, ethyl, n-propyl, i-propyl, n-butyl or i-butyl, cycloalkyl, preferably having 3 to 6 carbon atoms, or an aryl, preferably having 6 to 12 carbon atoms, for example, phenyl, 4-tolyl, 4-methoxyphenyl, 4-chlorophenyl, 4-bromophenyl, 4-nitrophenyl, naphthyl or biphenyl.

(2) $R''SO_2N(CH_3)N(CH_3)SO_2R''$, namely 1,2-bis(sulfonyl)-1,2-dimethylhydrazines, wherein R'' is an alkyl having 1 to 10 carbon atoms, preferably 1 to 6 carbon atoms and preferably methyl, ethyl, n-propyl, i-propyl, n-butyl or i-butyl, cycloalkyl, preferably having 3 to 6 carbon atoms, or an aryl, preferably having 6 to 12 carbon atoms, for example, phenyl, 4-tolyl, 4-methoxyphenyl, 4-chlorophenyl, 4-bromophenyl, 4-nitrophenyl, naphthyl or biphenyl.

The present invention further relates to a method of treating trypanosomiasis in patients, e.g., warm-blooded animals, such as humans, horses, sheep, goats, swine, camels or cattle, by administering to such patients a trypanocidal effective amount of a methylating agent as described above.

The present invention also concerns a method of treating trypansomiasis in a warm-blooded animal patient comprising administering to said patient a trypanocidal effective amount of a compound capable of generating a methylating agent of the formula $CH_3N=NX'$, wherein X' is a leaving group, e.g., OH or $SO_2R'''$, wherein R''' is an alkyl or an aryl, more particularly an unsubstituted or substituted alkyl having 1 to 10, preferably 1 to 6, carbon atoms or an unsubstituted or substituted aryl, including other species capable of generating methyl radicals ($CH_3\bullet$), diazomethane ($CH_2N_2$) or methyldiazonium ($CH_3N_2^+$). Non-limiting examples of such compounds which generate $CH_3N=NX'$ include N-methyl-N-nitrosourea, 5-(3,3-dimethyl-1-triazenyl)-

1H-imidazole-4-carboxamide, streptozotocin and 1,2-bis(sulfonyl)-1-methylhydrazines.

Typical substituents for the substituted alkyl and substituted aryl for R', R" and R''' in the above formulas include halogen, e.g., chlorine, fluorine or bromine, hydroxy and nitro. Furthermore, the aryl can be substituted by $C_1$-$C_{10}$ alkyl or $C_1$-$C_{10}$ alkoxy.

The present invention is also directed to a method of treating cancer in a warm-blooded animal patient, e.g., human patient, comprising administering to such patient an antineoplastic effective amount of a methylating agent selected from the group consisting of (a) $R'SO_2N(CH_3)N(SO_2CH_3)_2$, wherein R' is an alkyl having 1 to 10 carbon atoms or an aryl, for example, phenyl, 4-tolyl, 4-methoxyphenyl, 4-chlorophenyl, 4-bromophenyl, 4-nitrophenyl, naphthyl or biphenyl, and (b) $R''SO_2N(CH_3)N(CH_3)SO_2R''$, wherein R" is an alkyl having 1 to 10 carbon atoms or an aryl, for example phenyl, 4-tolyl, 4-methoxyphenyl, 4-chlorophenyl, 4-bromophenyl, 4-nitrophenyl, naphthyl or biphenyl.

DETAILED DESCRIPTION OF THE INVENTION

Synthesis

1-Methyl-1,2,2-tris(methylsulfonyl)hydrazine was synthesized by reacting methylhydrazine with an excess of methanesulfonyl chloride in pyridine.

1,2-Bis(methylsulfonyl)-1,2-dimethylhydrazine was prepared by reacting methanesulfonyl chloride with 1,2-dimethylhydrazine dihydrochloride in approximately a 2:1 molar ratio in pyridine. 1-(2-Chloroethyl)-1,2,2-tris(methylsulfonyl)hydrazine was synthesized as shown in the following reaction scheme:

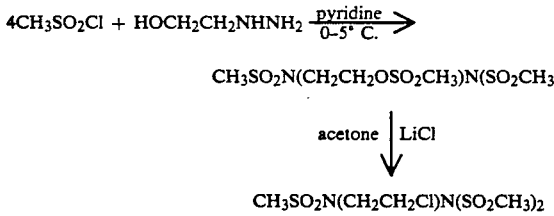

The use of lithium bromide and potassium iodide in lieu of lithium chloride in the second step gave the 2-bromoethyl and the 2-iodoethyl analogues, respectively. 1-Arylsulfonyl-1-(2-chloroethyl)-2,2-bis(methylsulfonyl)hydrazines were synthesized by reacting the corresponding 1-arylsulfonyl-1-(2-methylsulfonyloxy)ethyl-2,2-bis(methylsulfonyl)hydrazine with lithium chloride in acetone. The (methylsulfonyloxy)ethyl compound, in turn, was prepared by reacting the appropriate 1-arylsulfonyl-1-(2-hydroxyethyl)hydrazide with an excess of methanesulfonyl chloride in pyridine. The 1-arylsulfonyl-1-(2-hydroxyethyl)hydrazides were prepared by methodology analogous to that described by K. Shyam, R. T. Hrubiec, R. Furubayashi, L. A. Cosby and A. C. Sartorelli, *J. Med. Chem.*, 30, 2157–2161 (1987).

Mechanisms of Activation

The 1,2,2-tris(sulfonyl)-1-methylhydrazines are believed to undergo spontaneous hydrolysis in aqueous solutions at neutral pH to generate 1,2-bis(sulfonyl)-1-methylhydrazines as shown below.

$(CH_3SO_2)_2NN(CH_3)SO_2CH_3 + H_2O \longrightarrow$ $CH_3SO_2NHN(CH_3)SO_2CH_3 + CH_3SO_3H$ In the case of 1,2,2-tris(methylsulfonyl)-1-methylhydrazine, this reaction occurs slowly. A 50 μM solution of this compound hydrolyzes at an initial rate of 1% per minute in phosphate buffered saline (pH 7.6) at 37° C.

Hydrolysis is expected to occur preferentially at N-2 to generate the 1,2-bis(sulfonyl)-1-methylhydrazine. The sulfonic acid and 1,2-bis(sulfonyl)-1-methylhydrazine that are generated are both ionized under these conditions. The release of protons can be used to follow the decomposition of these and related compounds. The release of protons can be assayed by following the decrease in absorbance at 560 nm of a weakly buffered (1 mM potassium phosphate) phenol red (21 mg/l) solution; initial pH 7.6 at 37° C. The assay can be calibrated using HCl standards.

The 1,2-bis(sulfonyl)-1-methylhydrazine anions are believed to decompose under these conditions by a two-step process, generating the putative alkylating species $RSO_2N=NCH_3$ as an intermediate. The intermediate can methylate nucleophiles, such as water and other biomolecules as shown below.

$RSO_2^\ominus,ovs/N/$
$—N(CH_3)SO_2R \rightarrow RSO_2N=NCH_3 + RSO_2^-$ $RSO_2N=NCH_3 + H_2O \rightarrow RSO_2^- + N_2 + CH_3OH + H^+$ The reaction of 1,2-bis(sulfonyl)-1-methylhydrazine with water at pH 7.4–7.6 at 37° C. can be followed by proton release and/or methanol generation. Methanol generation can be assayed using alcohol oxidase and measuring the resultant $O_2$ consumption using a Gilson oxygraph. This assay can be calibrated using methanol standards. The reaction of 1,2-bis(sulfonyl)-1-methylhydrazine with water is relatively fast [a 50 μM solution of 1,2-bis(methylsulfonyl)-1-methylhydrazine decomposes at an initial rate of 12–15% per minute in phosphate buffered saline (pH 7.6) at 37° C.] compared to the hydrolysis of 1,2,2-tris(methylsulfonyl)-1-methylhydrazine. $RSO_2N=NMe$ may also decompose by a free radical mechanism to a smaller extent and methylate by the generation of methyl radicals.

The 1-(2-chloroethyl)-1,2,2-tris(methylsulfonyl)hydrazine would be expected to undergo hydrolysis and base-catalyzed elimination in a manner analogous to the 1,2,2-tris(sulfonyl)-1-methylhydrazines. The chloroethylating species generated in this case, $ClCH_2CH_2N=NSO_2CH_3$, would be expected to act as a bifunctional alkylating agent as shown below.

$ClCH_2CH_2N=NSO_2CH_3 + NuH \longrightarrow$ $ClCH_2CH_2Nu + CH_3SO_2^- + N_2 + H^+$ $\downarrow Nu'H$ $Nu'CH_2CH_2Nu,$ wherein Nu and Nu' are biological nucleophiles, e.g., primary or secondary amines, sulfhydryl groups or carboxy groups.

Compounds of the general structure R"SO$_2$N(CH$_3$)N(CH$_3$)SO$_2$R" may act as methylating agents by several mechanisms including:

(i) hydrolysis to generate 1,2-dimethylhydrazine followed by oxidation to give 1,2-dimethyldiazene as follows:

RSO$_2$N(CH$_3$)N(CH$_3$)SO$_2$R→CH$_3$NHNHCH$_3$→CH$_3$N=NCH$_3$

CH$_3$N=NCH$_3$→CH$_3$• + N$_2$ + CH$_3$•

(ii) N-demethylation to give 1,2-bis(sulfonyl)-1-methylhydrazine.

Formulations and Modes of Administration

The invention further provides pharmecutical compositions containing as an active ingredient the aforementioned sulfonylhydrazines, the aforementioned 1,2,2-tris(sulfonyl)-1-methylhydrazine, or the aforementioned 1,2-bis(sulfonyl)-1,2-dimethylhydrazine in the form of a sterile and/or physiologically isotonic aqueous solution.

The invention also provides a medicament in dosage unit form comprising the aforementioned sulfonylhydrazines, the aforementioned 1,2,2-tris(sulfonyl)-1-methylhydrazine, or the aforementioned 1,2-bis(sulfonyl)-1,2-dimethylhydrazine, all hereinafter referred to as the "active ingredient" or "active compound".

The invention also provides a medicament in the form of tablets (including lozenges and granules), caplets, dragees, capsules, pills, ampoules or suppositories comprising the aforementioned sulfonylhydrazine, the aforementioned 1,2,2-tris(sulfonyl)-1-methylhydrazine or the aforementioned 1,2-bis(sulfonyl)-1,2-dimethylhydrazine, all hereinafter referred to as the "active ingredient" or "active compound".

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of an active compound of the invention in association with a carrier and/or enclosed within an envelope. Whether the medicament contains a daily dose, or for example, a half, a third, or a quarter of a daily dose will depend on whether the medicament is to be administered once, or for example, twice, three times, or four times a day, respectively.

The pharmaceutical compositions according to the invention may, for example, take the form of suspensions, solutions and emulsions of the active ingredient in aqueous or non-aqueous diluents, syrups, granulates, or powders.

The diluents to be used in pharmaceutical compositions (e.g., granulates) adapted to be formed into tablets, dragees, capsules and pills may include one or more of the following: (a) fillers and extenders, e.g., starch, sugars, mannitol and silicic acid; (b) binding agents, e.g., carboxymethyl cellulose and other cellulose derivatives, aliginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules, caplets and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents such as solvents, solubilizing agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofuryl alcohol, polyethylene glycols and fatty acid esters of sorbitol or mixtures thereof.

For parenteral administration, solutions and emulsions should be sterile and, if appropriate, blood-isotonic.

The pharmaceutical compositions which are suspensions can contain the usual diluents, such as liquid diluents, e.g., water, ethyl alcohol, propylene glycol, surface-active agents (e.g., ethoxylated isostearyl alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain coloring agents and preservatives, as well as perfumes and flavoring additives (e.g., peppermint oil and eucalyptus oil) and sweetening agents (e.g., saccharin and aspartame).

The pharmaceutical compositions according to the invention generally contain from 0.5 to 90% of the active ingredient by weight of the total composition.

The pharmaceutical compositions and medicaments according to the invention can also contain other pharmaceutically active compounds.

The discrete coherent portions constituting a medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, may include a protective envelope which renders the portions of the medicament physically discrete and coherent.

The preferred daily dose for administration of the medicaments of the invention is 60 to 600 mg/square meter of body surface per day of active ingredient. Nevertheless, it can at times be necessary to deviate from these dosage levels, and in particular to do so as a function of the nature of the human or animal subject to be treated, the individual reaction of this subject to the treatment, the type of formulation in which the active ingredient is administered, the mode in which the administration is carried out and the point in the progress of the disease or interval at which it is to be administered. Thus, it may in some cases suffice to use less than the above-mentioned minimum dosage rate, while in other cases the upper limit mentioned must be exceeded to achieve the desired results. Where larger amounts are administered, it may be advisable to divide these into several individual administrations over the course of a day.

The production of the above-mentioned pharmaceutical compositions and medicaments is carried out by any method known in the art, for example, by mixing the active ingredient(s) with the diluent(s) to form a pharmaceutical composition (e.g., a granulate) and then forming the composition into the medicament (e.g., tablets).

This invention provides a method for treating the above-mentioned diseases in warm-blooded animals, which comprises administering to the animals an active compound of the invention alone or in admixture with a diluent or in the form of a medicament according to the invention.

It is envisaged that the active compounds will be administered perorally, parenterally (e.g., intramuscularly, intraperitoneally, subcutaneously, or intravenously), rectally, or locally, preferably orally or parenterally, especially perlingually or intravenously. Preferred pharmaceutical compositions and medicaments are, therefore, those adapted for administration, such as oral or parenteral administration. Administration in the methods of the invention are preferably oral administration or parenteral administration.

Treatment of Trypanosomiasis

One aspect of the present invention is the treatment of trypanosomiasis by administration of methylating agents. Such methylating agents are effective against *T.rhodesiense* and *T.gambiense*, which cause fatal diseases in man, and also against *T.brucei*, *T.evansi* and *T.equiperdum*, which are of veterinary importance (C. A. Hoare, *Adv. Parasitol.*, 5, 47-91 (1967)).

Some methylating agents for use in the present invention are described in K. Shyam, R. T. Hrubiec, R. Furubayashi, L. A. Cosby and A. C. Sartorelli, *J. Med. Chem.*, 30, 2157-2161 (1987).

Non-limiting examples of methylating agents for use in the present invention include $CH_3NHNH_2$, $CH_3NHNHCH_3$, $CH_3SO_2N(CH_3)NHSO_2CH_3$, $CH_3SO_2N(CH_3)NHSO_2C_6H_4$—p—$OCH_3$, $(CH_3)_2SO_4$, $CH_3SO_2OCH_3$, N-methyl-N-nitrosourea, procarbazine, 5-(3,3-dimethyl-1-triazenyl)-1H-imidazole-4-carboxamide and streptozotocin.

Thirty-day "cures" of mice bearing *T.rhodesiense* were obtained with some of these agents at single dose levels which produced no overt signs of toxicity.

In general, compounds lacking a reactive methyl group, but structurally identical to the corresponding N-methyl analogues in all other respects, or containing the methyl group, but lacking good leaving groups, are inactive as trypanocides (see Table III hereinbelow). The kinetics of the loss of activity of methylating agents upon the "aging" of an aqueous solution correlates well with the kinetics of methanol generation, a measure of the spontaneous breakdown of these agents to generate the reactive methyl group. These findings provide strong evidence that methylation is essential for the observed biological activity of these compounds.

Methylating agents appear to have two major effects on trypanosomes, depending upon the dose level. At high levels, cytokinesis appears to be inhibited almost immediately and the cells are transformed into transitional forms containing multiple nuclei and kinetoplasts. These cells disappear from the bloodstream in 48 to 72 hours. When administered at repetitive low doses, methylating agents induce the entire population to differentiate into short-stumpy forms (short-stumpy forms cannot differentiate further unless they are taken up by a feeding tsetse fly or placed in appropriate culture conditions), as judged by morphology, NADH diaphorase positivity and other biochemical and physiological criteria. Short-stumpy forms are non-dividing differentiated cells and are not infective to the mammalian host. The latter property may make these agents useful biochemical tools in the study of differentiation in trypanosomes, since, with these compounds, it is possible to induce the entire population of trypanosomes to differentiate in a moderately synchronous manner and through this approach early events in the differentiation process can be studied. Both single high dose regimens and repetitive low doses can result in cures using a number of the methylating agents described herein.

DFMO has also been shown to induce differentiation in *T. brucei* (B. F. Giffin, P. P. McCann, A. J. Bitanti and C. J. Bacchi, *J. Protozool.*, 33, 238-243 (1986)). This effect is generally attributed to the depletion of polyamines. DFMO, however, also causes a 1000-fold increase in decarboxylated S-adenosylmethionine (DSAM) and S-adenosylmethionine (SAM) (A. H. Fairlamb, G. B. Henderson, C. J. Bacchi and A. Cerami, *Mol. Biochem. Parasitol.* 7, 209-225 (1983)). These latter metabolites are weak chemical methylating agents and, therefore, may be in part responsible for the differentiating action of DFMO. The depletion of polyamines and trypanothione as a result of the DFMO treatment may potentiate the actions of SAM and DSAM as methylating agents by decreasing the levels of competing nucleophiles. Depletion of polyamines may also make the nucleic acids more susceptible to methylation (R. L. Wurdeman and B. Gold, *Chemical Res. Toxicol.*, 1, 146-147 (1988)). SAM is also the methyl donor used by many methylases; therefore, enzymatically mediated methylation reactions may also be affected.

Orally active trypanocidal agents are desirable, since in areas where trypanosomiasis is endemic, other routes of drug administration frequently present problems. Although methylating agents in general are mutagenic, in cases of multi-drug resistant trypanosomiasis which have failed to respond to existing therapies, these compounds may be extremely effective.

The distinct advantages of methylating agents over existing trypanocides include (a) high therapeutic indices, (b) oral activity, (c) novel mechanism of action, (d) broad-spectrum antitrypanosomal activity, and (e) favorable pharmacokinetics which make these compounds candidates for both agricultural and clinical development.

The invention will now be described with reference to the following non-limiting examples.

EXAMPLES

Melting points were determined on a Thomas-Hoover capillary melting point apparatus and are uncorrected. Proton magnetic resonance spectra were recorded on a Varian EM-390 spectrometer with Me$_4$Si as an internal standard. Elemental analyses were performed by the Baron Consulting Co. (Orange, CT.) and the data were within 0.4% of the theoretical values.

EXAMPLES 1 to 6

A.

1-(2-Methylsulfonyloxy)ethyl-1,2,2-tris(sulfonyl)hydrazines

Example 1

Preparation of 1-(2-methylsulfonyloxy)ethyl-1,2,2-tris(methylsulfonyl)hydrazine

To an ice-cold stirred solution of 2-hydroxyethylhydrazine (6.08 g, 0.08 mol) in dry pyridine (40 ml) was added methanesulfonyl chloride (41.2 g, 0.36 mol) dropwise, while maintaining the temperature between 0° and 5° C. After keeping the reaction mixture stirred at this temperature range for an additional 3 hours, it was left in a freezer ($-10°$ C.) for 48 hours. It was then triturated with a mixture of ice and concentrated hydrochloric acid (100 ml, 1:1, v/v). A thick semi-solid separated and settled at the bottom of the flask. Sometimes a solid separated, which was filtered and treated as described below. The clear supernatant was carefully decanted and the semi-solid was warmed to 60° C. in glacial acetic acid (150 ml) and was cooled to 5° C. The solid that separated was filtered, washed with cold glacial acetic acid (20 ml), dried and recrystallized from ethanol-acetone (1:3, v/v) using Norit A as a decolorizing agent to give 9.6 g (31%) of the title compound: m.p. 160°–162° C.; anal.($C_6H_{16}N_2O_9S_4$) C,H,N: $^1$H NMR (acetone-d$_6$) δ 4.5 and 4.1 (2t, 4H, CH$_2$CH$_2$), 3.6 [s, 6H, N$^2$(SO$_2$CH$_3$)$_2$], 3.3 [s, 3H, N$^1$SO$_2$CH$_3$], 3.2 [s, 3H, OSO$_2$CH$_3$].

Example 2

Preparation of 2,2-bis(methylsulfonyl)-1-(2-methylsulfonyloxy)ethyl-1-(4-toluenesulfonyl)hydrazine To an ice-cold stirred mixture of 1-(2-hydroxyethyl)-1-(4-toluenesulfonyl)hydrazide (6.9 g, 0.03 mol) and dry pyridine (12 ml) was added methanesulfonyl chloride (14.1 g, 0.12 mol) dropwise, while maintaining the temperature between 0° and 10° C. After an additional 3 hours of stirring at this temperature range, the reaction mixture was left in a freezer ($-10°$ C.) for 48 hours. It was then triturated with a mixture of ice and concentrated hydrochloric acid (100 ml, 1:1, v/v). A thick semi-solid separated and settled to the bottom of the flask. The clear supernatant was carefully decanted and the residue was boiled with ethanol (100 ml). A solid separated that was filtered while the ethanol mixture was still hot, washed with ethanol and dried. It was recrystallized from a mixture of ethanol and acetone (Norit A) to give 4.7 g (34%) of the title compound: m.p. 153°–155° C.; anal. ($C_{12}H_{20}N_2O_9S_4$) C,H,N; $^1$H NMR (acetone-d$_6$) δ 7.9 and 7.4 (2d, 4H, aromatic H), 4.4 and 4.0 (2t, 4H, CH$_2$CH$_2$), 3.6 [s, 6H, N(SO$_2$CH$_3$)$_2$], 3.0 [s, 3H, OSO$_2$CH$_3$] and 2.4 [s, 3H, ArCH$_3$].

Example 3

Preparation of 2,2-bis(methylsulfonyl)-1-(2-methylsulfonyloxy)ethyl-1-phenylsulfonylhydrazine 1-(2-Hydroxyethyl)-1-phenylsulfonylhydrazide (10.8 g, 0.05 mol) and methanesulfonyl chloride (29.6 g, 0.26 mol were reacted in dry pyridine (25 ml) and the product was isolated in a manner identical to that described for 2,2-bis(methylsulfonyl)-1-(2-methylsulfonyloxy)ethyl-1-(4-toluenesulfonyl)hydrazine (see Example 2 above): yield, 3.1 g (14%); m.p. 107°–108° C.; anal. ($C_{11}H_{18}N_2O_9S_4$) C,H,N; $^1$H NMR (acetone-d$_6$) δ 8.0 and 7.7 (d and m, 5H, aromatic H), 4.3 and 4.0 (2t, 4H, CH$_2$CH$_2$), 3.6 [s, 6H, N(SO$_2$CH$_3$)$_2$], 3.0 (s, 3H, OSO$_2$CH$_3$).

Example 4

Preparation of 2,2-bis(methylsulfonyl))-1-(2-methylsulfonyloxy)ethyl-1-[(4-methoxyphenyl)sulfonyl]hydrazine To an ice-cold stirred mixture of 1-(2-hydroxyethyl)-1-[4-methoxyphenyl)sulfonyl]hydrazide (10.0 g, 0.04 mol) and dry pyridine (25 ml) was added methanesulfonyl chloride (29.6 g, 0.26 mol) in portions, while maintaining the temperature between 0° and 5° C. After an additional 2 hours of stirring at this temperature range, the reaction mixture was left in a freezer ($-10°$ C.) for 48 hours. It was then triturated with a mixture of ice and concentrated hydrochloric acid (100 ml, 1:1, v/v), the clear supernatant was decanted and the thick semi-solid that separated was boiled with ethanol (100 ml) and cooled to 5° C. A yellow solid separated that was stirred with methylene chloride (200 ml) and filtered. The filtrate was evaporated to dryness in vacuo to give the crude title compound, which was recrystallized from a mixture of ethanol and acetone (Norit A): yield, 6.7 g (34%); m.p. 144°–145° C.; anal. ($C_{12}H_{20}N_2O_{10}S_4$) C,H,N; $^1$H NMR (acetone-d$_6$) δ 7.9 and 7.1 (2d, 4H, aromatic H), 4.3 and 4.0 (2t, 4H, CH$_2$CH$_2$), 3.9 [s, 3H, OCH$_3$], 3.6 [s, 6H, N(SO$_2$CH$_3$)$_2$], 3.0 [s, 3H, OSO$_2$CH$_3$].

Example 5

Preparation of 2,2-bis(methylsulfonyl)-1-[(4-chlorophenyl)sulfonyl]-1-(2-methylsulfonyloxy)ethylhydrazine To an ice-cold stirred mixture of 1-[(4-chlorophenyl)sulfonyl]-1-(2-hydroxyethyl)hydrazide (12.5 g, 0.05 mol) in dry pyridine (20 ml) was added methanesulfonyl chloride (23.68 g, 0.21 mol) dropwise, while maintaining the temperature between 0° and 10° C. After an additional 2 hours of stirring at this temperature range, the reaction mixture was left in the freezer ($-10°$ C.) for 48 hours. It was then triturated with a mixture of ice and concentrated hydrochloric acid (100 ml, 1:1, v/v). The solid that separated was filtered, stirred with chloroform (300 ml) for 10 minutes, treated with Norit A and filtered. On evaporation of the filtrate to dryness in vacuo a solid was obtained that was recrystallized from ethyl acetate-petroleum ether (Norit A) to give 6.3 g (26%) of the title compound: m.p. 152°–153° C.; anal. ($C_{11}H_{17}ClN_2O_9S_4$) C,H,N: $^1$H NMR (acetone-d$_6$) δ 8.1 and 7.7 (2d, 4H, aromatic H), 4.5 and 4.1 (2t, 4H, CH$_2$CH$_2$), 3.6 [s, 6H, N(SO$_2$CH$_3$)$_2$], 3.1 [s, 3H, OSO$_2$CH$_3$].

Example 6

Preparation of
2,2-bis(methylsulfonyl)-1-[(4-bromophenyl)sulfonyl]-1-(2-methylsulfonyloxy)ethylhydrazine This compound was prepared by reacting 1-[(4-bromophenyl)sulfonyl]-1-(2-hydroxyethyl)hydrazide (5.2 g, 0.018 mol) with methanesulfonyl chloride (9.0 g, 0.079 mol) in dry pyridine (15 ml) in a manner analogous to that described for 2,2-bis(methylsulfonyl)-1-[(4--chlorophenyl)sulfonyl]-1-(2-methylsulfonyloxy)ethylhydrazine (Example 5): yield, 2.5 g, (27%); m.p. 154°–155° C.; anal. (C$_{11}$H$_{17}$BrN$_2$O$_9$S$_4$) C,H,N; $^1$H NMR (acetone-d$_6$) δ 7.9–8.0 (2d, 4H, aromatic H), 4.4 and 4.1 (2t, 4H, CH$_2$CH$_2$), 3.6 [s, 6H, N(SO$_2$CH$_3$)$_2$], 3.0 [s, 3H, OSO$_2$CH$_3$].

EXAMPLES 7 TO 14

B. 1-(2-Haloethyl)-1,2,2-tris(sulfonyl)hydrazines

Example 7

Preparation of
1-(2-chloroethyl)-1,2,2-tris(methylsulfonyl)hydrazine

A mixture of 1-(2-methylsulfonyloxy)ethyl-1,2,2-tris(methylsulfonyl)hydrazine (2,0 g, 0.005 mol), lithium chloride (2.0 g, 0.047 mol) and dry acetone (50 ml) was heated under reflux for 96 hours. The reaction mixture was cooled to room temperature, filtered and the filtrate evaporated to dryness in vacuo. The residue was warmed with chloroform (100 ml) to 50° C., filtered and the filtrate was evaporated to dryness in vacuo. Recrystallization of the residue from ethanol gave 1.1 g (65%) of the title compound: m.p. 154°–155° C.; anal. (C$_5$H$_{13}$ClN$_2$O$_6$S$_3$) C,H,N; $^1$H NMR (CDCl$_3$) δ 3.6–4.0 (m, 4H, CH$_2$CH$_2$), 3.5 [s, 6H, N$^2$(SO$_2$CH$_3$)$_2$], 3.2 (s, 3H, N$^1$SO$_2$CH$_3$).

Example 8

Preparation of
1-(2-bromoethyl)-1,2,2-tris(methylsulfonyl)hydrazine 1-(2-Bromoethyl)-1,2,2-tris(methylsulfonyl)hydrazine was prepared in a manner analogous to that of the corresponding 2-chloroethyl analogue by reacting 1(2-methylsulfonyloxy)ethyl-1,2,2-tris(methylsulfonyl)hydrazine with lithium bromide in acetone for 48 hours: yield, 35%; m.p. 147°–148° C.; anal. (C$_5$H$_{13}$BrN$_2$O$_6$S$_3$) C,H,N; $^1$H NMR (CDCl$_3$) δ 4.0 and 3.6 (2t, 4H, CH$_2$CH$_2$), 3.5 [s, 6H, N$^2$(SO$_2$CH$_3$)$_2$] and 3.2 [s, 3H, N$^1$SO$_2$CH$_3$].

Example 9

Preparation of
1-(2-iodoethyl)-1,2,2-tris(methylsulfonyl)hydrazine 1-(2-Iodoethyl)-1,2,2-tris(methylsulfonyl)hydrazine was prepared in a manner analogous to that of the corresponding 2-chloroethyl analogue by reacting 1-(2-methylsulfonyloxy)ethyl-1,2,2-tris(methylsulfonyl)hydrazine with potassium iodide in acetone for 48 hours: yield, 66%; m.p. 136°–138° C.; anal. (C$_5$H$_{13}$IN$_2$O$_6$S$_3$) C,H,N; $^1$H NMR (CDCl$_3$) δ 4.0 and 3.4 (2t, 4H, CH$_2$CH$_2$), 3.5 [s, 6H, N$^2$(SO$_2$CH$_3$)$_2$] and 3.2 [s, 3H, N$^1$SO$_2$CH$_3$].

Example 10

Preparation of
2,2-bis(methylsulfonyl)-1-(2-chloroethyl)-1-(4-toluenesulfonyl)hydrazine A mixture of 2,2-bis(methylsulfonyl)-1-(2-methylsulfonyloxy)ethyl-1-(4-toluenesulfonyl)hydrazine (2.0 g, 0.0043 mol), dry lithium chloride (2.0 g, 0.047 mol) and dry acetone (50 ml) was heated under reflux for 4 days. The reaction mixture was filtered and the filtrate was evaporated to dryness in vacuo. The residue was warmed with chloroform (100 ml) to 40° C., filtered and the filtrate was evaporated to dryness. The residue was boiled with ethanol (150 ml) and cooled to 10° C. The unreacted sulfonate which crystallized was removed by filtration and the filtrate was evaporated to dryness in vacuo. The residue thus obtained was recrystallized from chloroform-petroleum ether (Norit A) to give 1.2 g (69%) of the title compound: m.p. 99°–101° C.; anal. (C$_{11}$H$_{17}$ClN$_2$O$_6$S$_3$) C,H,N; $^1$H NMR (CDCl$_3$) δ 7.9 and 7.4 (2d, 4H, aromatic H), 3.6–3.9 (m, 4H, CH$_2$CH$_2$), 3.5 [s, 6H, (SO$_2$CH$_3$)$_2$] and 2.4 [s, 3H, ArCH$_3$].

Example 11

Preparation of
2,2-bis(methylsulfonyl)-1-(2-chloroethyl)-1-phenylsulfonylhydrazine A mixture of 2,2-bis(methylsulfonyl)-1-(2-methylsulfonyloxy)ethyl-1-phenylsulfonylhydrazine (2.0 g, 0.0044 mol), dry lithium chloride (2.0 g, 0.047 mol) and dry acetone (50 ml) was heated under reflux for 5 days. The reaction mixture was filtered and the filtrate was evaporated to dryness in vacuo. To the residue was added chloroform (100 ml) and the mixture was stirred for 10 minutes and filtered. The filtrate was evaporated to dryness and the semi-solid residue obtained was dissolved by boiling in a minimum quantity of ethanol and was filtered. On cooling, the title compound was obtained as white crystals: yield, 0.68 g (39%); m.p. 114°–115° C.; anal. (C$_{10}$H$_{15}$ClN$_2$O$_6$S$_3$) C,H,N; $^1$H NMR (acetone-d$_6$) δ 8.0 and 7.7 (d and m, 5H, aromatic H), 3.6–4.0 (m, 4H, CH$_2$CH$_2$) and 3.6 [s, 6H, 2CH$_3$].

EXAMPLES 12 TO 14

The following 1-(2-chloroethyl)-1,2,2-tris(sulfonyl)hydrazines were synthesized using procedures similar to those described above:

Example 12

2,2-Bis(methylsulfonyl)-1-(2-chloroethyl)-1-[(4-methoxyphenyl)sulfonyl]hydrazine Yield, 68%; m.p. 109°–110° C.; anal. (C$_{11}$H$_{17}$ClN$_2$O$_7$S$_3$) C,H,N; $^1$H NMR (CDCl$_3$) δ 7.9 and 7.0 (2d, 4H, aromatic H), 3.9 (s, 3H, OCH$_3$), 3.5–3.8 (m, 4H, CH$_2$CH$_2$) and 3.5 [s, 6H, (SO$_2$CH$_3$)$_2$].

Example 13

2,2-Bis(methylsulfonyl)-1-(2-chloroethyl)-1-[(4-chlorophenyl)sulfonyl]hydrazine

Yield, 69%; m.p. 122°–123° C.; anal. (C$_{10}$H$_{14}$Cl$_2$N$_2$O$_6$S$_3$) C,H,N; $^1$H NMR (CDCl$_3$) δ 7.9 and 7.5 (2d, 4H, aromatic H), 3.6–4.0 (m, 4H, CH$_2$CH$_2$) and 3.5 [s, 6H, 2CH$_3$].

Example 14

2,2-Bis(methylsulfonyl)-1-[(4-bromophenyl)sulfonyl]-1-(2-chloroethyl)hydrazine

Yield, 45%; m.p. 117°–118° C.; anal. ($C_{10}H_{14}BrClN_2O_6S_3$) C,H,N; $^1$H NMR (acetone-$d_6$) δ 7.9–8.0 (2d, 4H, aromatic H), 3.7–4.1 (m, 4H, $CH_2CH_2$) and 3.6 [s, 6H, $2CH_3$].

Example 15

C. 1,2-Bis(methylsulfonyl)-1,2-dimethylhydrazine 1,2-Dimethylhydrazine dihydrochloride (2.6 g, 0.02 mol) was suspended in ice-cold dry pyridine (6 ml) and the mixture was stirred for 10 minutes. Methanesulfonyl chloride (5.0 g, 0.043 mol) was added in portions to this mixture, while maintaining the temperature between 0° and 10° C. After an additional 1 hour of stirring at 0° to 5° C., the reaction mixture was left in a freezer (−10° C.) overnight. The pH of the reaction mixture was adjusted to pH 1 with cold dilute hydrochloric acid. The solid that separated was filtered and recrystallized from ethanol (Norit A) to give 1.4 g (32%) of the title compound: m.p. 168°–169° C.; anal. ($C_4H_{12}N_2O_4S_2$) C,H,N; $^1$H NMR (CDCl$_3$) δ 3.1 [2s, 12H, $2(CH_3SO_2NCH_3)$].

Example 16

D. 1-Methyl-1,2,2-tris(methylsulfonyl)hydrazine

To an ice-cold stirred solution of methylhydrazine (4.6 g, 0.1 mol) in dry pyridine (30 ml) was added methanesulfonyl chloride (44.6 g, 0.39 mol) dropwise, while maintaining the temperature between 0° and 10° C. The reaction mixture was left in a freezer (−10° C.) for 2 days. It was then triturated with a mixture of ice and concentrated hydrochloric acid (1:1, v/v, 100 ml). The precipitate that formed was collected, washed with cold water and dried. This product was stirred with chloroform (200 ml) and filtered. The undissolved material, consisting mainly of 1,2-bis(methylsulfonyl)-1-methylhydrazine, was discarded and the filtrate was treated with decolorizing carbon, filtered and evaporated to dryness in vacuo to give a yellow solid, which was crystallized twice from ethanol (Norit A) to give 5.1 g (18%) of the title compound: m.p. 123°–124° C.; anal. ($C_4H_{12}N_2O_6S_3$) C,H,N; $^1$H NMR (acetone-$d_6$) δ 3.6 [s, 6H, $N^2(SO_2CH_3)_2$], 3.5 (s, 3H, N—$CH_3$), 3.2 (s, 3H, $N^1SO_2CH_3$).

Example 17

Antineoplastic Activity

The tumor-inhibitory properties of several compounds, e.g., 1,2-bis(methylsulfonyl)-1-methylhydrazine, 1-methyl-1,2,2-tris(methylsulfonyl)hydrazine, 1,2-bis(methylsulfonyl)-1,2-dimethylhydrazine and 1-(2-chloroethyl)-1,2,2-tris(methylsulfonyl)hydrazine were determined by measuring the effects of these agents on the survival time of mice bearing the L1210 leukemia as described by K. Shyam, L. A. Cosby, and A. C. Sartorelli, *J. Med. Chem.*, 28, 525–527 (1985). The results are summarized in Table I.

TABLE I

Effects of Sulfonylhydrazine Derivatives on the Survival Time of Mice Bearing the L1210 Leukemia

| Compound | Optimum effective Daily Dose, mg/kg$^a$ | AvΔ Wt, %$^b$ | % T/C$^c$ | 60-day cures, % |
|---|---|---|---|---|
| MeSO$_2$N(Me)N(SO$_2$Me)$_2$ | 150 | −7.7 | 186 | 0 |
| MeSO$_2$N(Me)N(Me)SO$_2$Me | 20 | −11.3 | 158 | 0 |
| MeSO$_2$N(Me)NHSO$_2$Me | 40 | −10.7 | 180 | 0 |
| MeSO$_2$N(CH$_2$CH$_2$Cl)N(SO$_2$Me)$_2$$^d$ | 60 | −7.2 | — | 100 |
| MeSO$_2$N(CH$_2$CH$_2$Br)N(SO$_2$Me)$_2$ | 150 | −2.0 | 213 | 0 |
| MeSO$_2$N(CH$_2$CH$_2$OSO$_2$Me)N(SO$_2$Me)$_2$ | 100 | −4.2 | 198 | 0 |
| MeSO$_2$N(CH$_2$CH$_2$I)N(SO$_2$Me)$_2$ | 150 | +8.0 | 110 | 0 |
| C$_6$H$_5$SO$_2$N(CH$_2$CH$_2$Cl)N(SO$_2$Me)$_2$ | 150 | +0.5 | 187 | 40 |
| MeO—4—C$_6$H$_4$SO$_2$N(CH$_2$CH$_2$Cl)N(SO$_2$Me)$_2$ | 200 | +5.9 | — | 100 |
| Me—4—C$_6$H$_4$SO$_2$N(CH$_2$CH$_2$Cl)N(SO$_2$Me)$_2$ | 150 | −12.0 | 215 | 60 |
| Cl—4—C$_6$H$_4$SO$_2$N(CH$_2$CH$_2$Cl)N(SO$_2$Me)$_2$ | 200 | −3.4 | 203 | 60 |
| Br—4—C$_6$H$_4$SO$_2$N(CH$_2$CH$_2$Cl)N(SO$_2$Me)$_2$ | 150 | +0.9 | 241 | 60 |

$^a$Administered once daily for 6 consecutive days, beginning 24 hours after tumor transplantation with 5–10 animals being used per group.
$^b$Average change in body weight from onset to termination of therapy.
$^c$% T/C = average survival time of treated/control animals × 100.
$^d$% T/C vs. P-388 leukemia = 218 (80% 60-day cures) at 60 mg/kg/day The methylating agents displayed considerable activity against this tumor and the chloroethylating agent [MeSO$_2$N(CH$_2$CH$_2$Cl)N(SO$_2$Me)$_2$] was exceedingly active, giving 60-day "cures" of the L1210 leukemia at levels of 40 and 60 mg/kg per day x 6. Replacement of the chloroethyl group in MeSO$_2$N(CH$_2$CH$_2$Cl)N(SO$_2$Me)$_2$ by bromoethyl or methylsulfonyloxyethyl resulted in retention of activity against the L1210 leukemia, the compounds giving maximum % T/C values of 213 and 198 percent, respectively. Activity was abolished when the chloroethyl group was replaced by iodoethyl.

A single intraperitoneal dose of 1.2 g/kg or six daily intraperitoneal doses of 200 mg/kg of MeSO$_2$N(CH$_2$CH$_2$Cl)N(SO$_2$Me)$_2$ produced no lethality in normal mice. Thus, the relatively great efficacy of this compound against the L1210 and P-388 leukemias and its relative lack of toxicity makes it an agent of significant promise.

Example 18

Trypanocidal Activity

The trypanocidal properties of several methylating agents including MeSO$_2$N(Me)N(SO$_2$Me)$_2$ and MeSO$_2$N(Me)N(Me)SO$_2$Me were determined by measuring their effects on the survival time of CD-1 mice infected with *T. rhodesiense* (Y Tat 1.1), a pleiomorphic strain that produces a non-replapsing disease in mice. The level of parasites in the bloodstream and body fluids increases by approximately 10-fold per day and the animals die when the parasite burden exceeds 1 to 2×10$^9$ cells/ml. Infection with a single viable parasite will kill a mouse in approximately 9 to 10 days.

Mice were infected ip with approximately $10^6$ trypanosomes/mouse in phosphate buffered saline containing glucose. This level of parasites produces death in 4 days post-infection. These mice were treated (ip) with a single dose of drug dissolved in the appropriate vehicle 3 days after infection, when the parasitemia was 1 to $3 \times 10^8$ cells/ml of blood and the mice, if untreated, would survive for only 24 additional hours. The number of days the mice survived beyond that of the untreated controls was used as a measure of trypanocidal activity. The level of parasitemia in treated mice was measured at regular intervals to distinguish between parasite-related and drug toxicity-related deaths. No toxic deaths were observed. Mice that survived for 30 days without detectable parasitemias were considered cured. The effects of a single dose of various methylating agents on the survival time of trypanosome-bearing mice are summarized in Table II.

TABLE II

Effects of Methylating and Ethylating Agents on the Survival Time of Mice Bearing T. rhodesiense

| Compound | Dose (mmol/kg) | Mean Extension of Life (Days) |
|---|---|---|
| MeNHNH$_2$[a] | 0.5 | 1 |
| MeNHNHMe[a] | 0.2 | 4.3 |
| EtNHNHEt[a] | 0.2 | 0 |
| MeSO$_2$N(Me)NHSO$_2$Me[b] | 0.2 | 11.8 |
| MeSO$_2$N(Me)NHSO$_2$C$_6$H$_4$-p-OMe[b] | 0.2 | 4.5 |
| PhSO$_2$N(Me)NHSO$_2$Ph[b] | 0.2 | 5.0 |
| MeSO$_2$N(Me)N(SO$_2$Me)$_2$[b] | 0.2 | 7.7 |
|  | 1.0 | 100% cure |
| MeSO$_2$N(Me)N(Me)SO$_2$Me[b] | 0.2 | 25% cure 9.7 for relapsing animals |
| Me$_2$SO$_4$[b] | 0.2 | 3.0 |
| Et$_2$SO$_4$[b] | 0.2 | 0 |
| MeSO$_2$OMe[b] | 0.2 | 1.0 |
| N-Methyl-N-nitrosourea[b] | 0.2 | 8.0 |
| Procarbazine[a] | 0.2 | 5.0 |
| DTIC[a] | 0.2 | 6.0 |
| Streptozotocin[a] | 0.2 | 4.3 |

[a]Drug that was administered was dissolved in 0.5 ml of phosphate buffered saline containing glucose.
[b]Drug that was administered was dissolved in 0.05 ml of DMSO.

As mentioned above, compounds lacking a reactive methyl group(s), but structurally identical in all other respects, or containing the reactive methyl group(s) but lacking good leaving groups, were inactive and failed to generate methanol in phosphate buffered saline (Table III).

TABLE III

Structural Requirements for Antitrypanosomal Activity

| Compound Administered in 0.05 ml of DMSO | Mean Extension of Life (Days) | Relative Methanol Generation in vitro |
|---|---|---|
| PhSO$_2$N(Me)NHSO$_2$Ph | 5 | 1.0 |
| PhSO$_2$NHNHSO$_2$Ph | 0 | 0 |
| PhCON(Me)NHCOPh | 0 | 0 |

Methanol was produced by these agents in aqueous solutions free from strong competing nucleophiles. Formation of this alcohol was used as a measure of the rate of spontaneous breakdown of these compounds to generate reactive methyl groups. When aqueous buffered (pH 7.6) solutions of 1,2-bis(methylsulfonyl)-1-methylhydrazine were assayed over time for the formation of methanol, no further alcohol was generated after 15 minutes, indicating that decomposition was complete within this time period. This result correlated with the loss of biological activity upon aging of equivalent solutions, where essentially all antiparasitic activity was lost after aging for 15 minutes, (i.e., 0, 21, 73 and 97% of the antitrypanosomal activity was lost after 0, 1, 5 and 15 minutes of aging, respectively). These findings provide strong evidence that methylation is essential for the observed biological activity of these compounds. In support of this hypothesis, a number of structurally unrelated methylating agents, but not ethylating agents were found to have significant biological activity (Table II).

The absence of clear-cut structure-activity relationships is probably due to the large number of variables introduced in vivo test systems and may reflect variation in parameters other than stability and rate of generation of the alkylating species.

A representative agent, 1,2-bis(methylsulfonyl)-1-methylhydrazine, was also tested against several other trypanosoma species. Activity has been demonstrated against T. gambiense which, like T. rhodesiense, causes a fatal disease in man, and against T. brucei brucei, T. evansi and T. equiperdum, which are species of veterinary importance.

The therapeutic indices of some of the invented compounds are significantly greater than that of the antineoplastic agents tested for antitrypanosomal activity; for example, cures are obtained with 1,2,2-tris(methylsulfonyl)-1-methylhydrazine at approximately 10% of the LD$_{50}$, whereas animals given streptozotocin at 50% of the published LD$_{50}$ survived for only 4 to 5 days longer than the control animals. Preliminary results indicate that 1,2-bis(methylsulfonyl)-1-methylhydrazine, 1,2,2-tris(methylsulfonyl)-1-methylhydrazine and 1,2-bis(methylsulfonyl)-1,2-dimethylhydrazine have comparable activity to that reported in Table II when administered orally in aqueous solutions. The decomposition of 1,2-bis(methylsulfonyl)-1-methylhydrazine in aqueous solutions can be inhibited by dosing in acidified solutions. Orally active trypanocidal agents are desirable since, in areas where trypanosomiasis is endemic, other routes of drug administration frequently present problems.

It will be appreciated that the instant specification and claims are set forth by way of illustration and not limitation, and that various modifications and changes may be made without departing from the spirit and scope of the present invention.

What is claimed is:

1. A pharmaceutical composition comprising as an active ingredient a trypanocidal effective amount of 1,2,2-tris(sulfonyl)-1-methylhydrazine of the formula R'SO$_2$N(CH$_3$)N(SO$_2$CH$_3$)$_2$, wherein R' is an alkyl having 1 to 10 carbon atoms or an aryl, in admixture with a solid, liquid, or liquefied gaseous diluent.

2. A pharmaceutical composition according to claim 1 in the form of a sterile physiologically isotonic aqueous solution.

3. A pharmaceutical composition according to claim 1, in the form of a tablet, pill, dragee, capsule, ampoule, or suppository.

4. A pharmaceutical composition comprising as an active ingredient a trypanocidal effective amount of 1,2-bis(sulfonyl)-1,2-dimethylhydrazine of the formula R"SO$_2$N(CH$_3$)N(CH$_3$)SO$_2$R", wherein R" is an alkyl having 1 to 10 carbon atoms or an aryl, in admixture with a solid, liquid, or liquefied gaseous diluent.

5. A pharmaceutical composition according to claim 4 in the form of a sterile physiologically isotonic aqueous solution.

6. A pharmaceutical composition according to claim 4, in the form of a tablet, pill, dragee, capsule, ampoule, or suppository.

7. A method of treating trypanosomiasis in a warm-blooded animal patient comprising administering to said patient a trypanocidal effective amount of a methylating agent, wherein the methylating agent is selected from the group consisting of
(a) $R'SO_2N(CH_3)N(SO_2CH_3)_2$, wherein $R'$ is an alkyl having 1 to 10 carbon atoms or an aryl and
(b) $R''SO_2N(CH_3)N(CH_3)SO_2R''$, wherein $R''$ is an alkyl having 1 to 10 carbon atoms or an aryl.

* * * * *